United States Patent [19]
Gould

[11] Patent Number: 5,865,818
[45] Date of Patent: Feb. 2, 1999

[54] DUAL FUNCTION SYRINGE AND BLUNT ASSEMBLY

[76] Inventor: Vincent G. Gould, 15 Scenic Dr., Westminster, Mass. 01473

[21] Appl. No.: 934,546

[22] Filed: Sep. 19, 1997

Related U.S. Application Data

[63] Continuation of Ser. No. 492,679, Jun. 20, 1995, abandoned.

[51] Int. Cl.⁶ .................................................. A61M 25/00
[52] U.S. Cl. .......................... 604/283; 604/187; 604/241; 604/905
[58] Field of Search ...................................... 604/283, 905

[56] References Cited

U.S. PATENT DOCUMENTS

| | | |
|---|---|---|
| 2,755,801 | 7/1956 | Morando ................................. 128/221 |
| 3,895,633 | 7/1975 | Bartner et al. . |
| 4,723,945 | 2/1988 | Theiling . |
| 4,816,020 | 3/1989 | Brownell ................................... 604/97 |
| 5,112,318 | 5/1992 | Novacek et al. ......................... 604/240 |
| 5,135,514 | 8/1992 | Kimber . |
| 5,304,154 | 4/1994 | Gloyer et al. ............................ 604/240 |
| 5,360,404 | 11/1994 | Novacek et al. ........................ 604/110 |
| 5,382,241 | 1/1995 | Choudhury et al. . |
| 5,389,086 | 2/1995 | Attermeier et al. . |

FOREIGN PATENT DOCUMENTS

| | | |
|---|---|---|
| 9007946 | 7/1990 | WIPO . |
| PCT 9007946 | 7/1990 | WIPO . |

OTHER PUBLICATIONS

Advetrisement for Tubex® (Blunt Pointe Sterile Cartridge Unit)—1 page.
Advertisement for Tubex® (Closed Injection System) (Sterile Cartridge Unit)—Wyeth–Ayerst Laboratories TU:372R—Feb. 1994—1 page.
Advertisement for Carpuject® and Carpuject® with Luer Lock (Sterile Cartridge–Needle Unit)—1995 Sanofi Winthrop Pharmaceuticals—6 pages.

Packaging from Monoject® Lifeshield® Blunt Cannulas—Polypropylene Hub; Stainless Sttel Cannula Attached with Epoxy Type Adhesive—Sherwood Medical, St. Louis, MO 63103, Reorder No. 8881–202017—1 page.

*Health Devices,* double issue, Aug.–Sep. 1994, vol. 23, No. 8–9 Needlestick–prevention Devices, ECRI, 5200 Butler Pike, Plymouth Meeting, PA 19362—pp. 315–358.

Sanofi Winthrop Product Release, dated Mar. 1995 (6 pages).

*Primary Examiner*—Wynn Wood Coggins
*Assistant Examiner*—Deborah Blyveis
*Attorney, Agent, or Firm*—Banner & Witcoff Ltd

[57] ABSTRACT

A medication injector assembly has dual functionality in that it can be configured as a needle syringe injector for intramuscular injections and the like or as a blunt injector for injection at a Y-site in an intravenous line and the like. A cartridge for holding a volume of injectable liquid medication has an injector fitting integral with the cartridge at one end. The injector fitting forms a blunt, elongate injection tip suitable for use as a blunt injector at the Y-site. The cartridge has a second, open end for receiving a hand-operable plunger for forcing the injectable liquid from the cartridge through the injection tip. A needle subassembly has an injection needle integrally mounted to a base. The needle subassembly has a socket to form a fluid-tight, operationally secure interconnection with the injection tip of the injector fitting, and means for locking attachment to the injector fitting.

10 Claims, 4 Drawing Sheets

DUAL FUNCTION SYRINGE AND BLUNT ASSEMBLY

This application is a continuation of application Ser. No. 08/492,679, filed Jun. 20, 1995, now abandoned.

INTRODUCTION

The present invention is directed to a medication injector assembly having dual functionality as a needle syringe for intramuscular injections and the like, and as a blunt injector for injections via a Y-fitting in an intravenous line and the like.

BACKGROUND

Currently, hospitals and other medical facilities stock syringes for intramuscular injections. The syringe assembly typically includes a vial or cartridge which is open-ended at one end, a hand-operable plunger which is received into the cartridge at the open end, and a needle or "sharp" subassembly. The needle subassembly typically includes the thin, elongate, hollow bore needle secured in a fluid-tight fashion to a base. The needle subassembly may be provided separately from the cartridge. The needle base can be attached to a fluid port at the end of the cartridge opposite its open end. In that regard, it is of growing importance that the needle subassembly attach to the cartridge with a positive locking feature to prevent its disengagement from the cartridge during or after use in the patient, for example, as the needle is withdrawn from the patient. At this time the needle is contaminated and should not be handled directly by the nurse, doctor, or others. While a friction fit has been employed to attach the needle subassembly to the cartridge, more preferably a positive lock such as a Luer Lock (trademark) threaded connection or the like is required.

Many hospitals and other medical facilities also now stock so-called blunt injectors. Blunt injectors employ a cartridge fitted with a hand-operable plunger and a blunt-ended injection tip. The injection tip is elongate, although typically much shorter than a standard syringe needle. It is adapted to be inserted into a self-sealing injection port at a Y-fitting in an intravenous line. An intravenous line extending from a needle which is semi-permanently installed in the patient for delivering medication, saline, etc. has a Y-fitting at some distance from the needle to present an auxiliary injection site. The blunt injector is inserted through a self-sealing membrane at such auxiliary injection site. The self-sealing membrane is slit or otherwise adapted to receive the blunt injector tip. Since a sharp needle is not needed for such injections, a blunt injector tip is used to enhance the safety of the medication administrator.

It is a significant cost burden that hospitals and other medical facilities must maintain a stock supply of both needle syringe injectors and blunt injectors. This duplicate stocking of two different types of injector assemblies involves not only undesirably high inventory costs, but also larger than desirable storage space requirements. Moreover, injection assembly cartridges often are stocked pre-filled with medication. In those cases, the cost of the medication may greatly exceed the cost of the injector assembly. Hence, redundant stocking of both blunt and sharp injector assemblies involves even much greater inventory costs. It is an object of the invention to reduce the inventory redundancy of stocking of both blunt and sharp injector assemblies. Additional objects of the invention will become apparent from the following disclosure of the invention and detailed discussion of certain preferred embodiments.

SUMMARY

In accordance with a first aspect, an injector assembly is provided which can be used either as a blunt injector, suitable, for example, for injecting medication into a Y-fitting in an intravenous line and the like, or in an alternative arrangement as a sharp injector for direct intramuscular injections and the like. A cartridge is provided which optionally is pre-filled with injectable medication. The cartridge typically is tubular in shape and in accordance with known principles of operation has an open end which receives a hand-operable plunger. It will be understood by those skilled in the art, that is, those who are knowledgeable and experienced in this area of technology, that the cartridge is said to be open-ended in the sense that it can receive the plunger. If it is pre-filled, then the cartridge will have a moveable stopper at the open end to cooperate with the cartridge in containing the medication. In that case, the plunger is received into the open end of the cartridge to push against the stopper at the time of injecting the medication. An injector fitting on the cartridge provides a blunt injection tip or port for injection at an intravenous ("IV") Y-fitting and the like, and also securely receives attachment of a needle subassembly for intramuscular injection and the like. More specifically, without attachment of the needle subassembly, the cartridge with its injector fitting and plunger, referred to here sometimes as a blunt injector subassembly, is fully functional as a blunt injector. The injector fitting thus provides an elongated, blunt injection tip, that is an outlet port for medication from the cartridge, which is blunt but sufficiently extended for reliable, secure use in the known manner at an IV Y-fitting and the like. The injector fitting in addition, however, is attachable to a separate needle subassembly to form therewith a secure attachment in which the injection tip has fluid-tight communication with the needle. The attachment is secure in the sense that the resulting assembly is suitable for use in the customary way of needle syringes, in normal and/or emergency circumstances. More specifically, it remains correctly assembled with an operationally secure interconnection to the needle subassembly. With respect to the interconnection being operationally secure, in addition to the ordinary meaning, the injection tip of the injector fitting is received into a correspondingly configured chamber in a base of the needle subassembly with substantially no peripheral air pocket in communication with the fluid flow during injection. Air in any such peripheral air pockets may not be evacuated by initial plunger advancement outside the patient (as is air directly in the line of flow, e.g., in the central bore holes of the blunt tip and needle). Air bubbles may, however, be squeezed out of such a peripheral air pocket under the stresses and movement of actual injection, becoming entrained in the flow of medication and possibly entering the patient with adverse medical effect. Most advantageously, the cartridge injector fitting comprises means for positive locking attachment of the needle subassembly, for example, a Luer-lock (trademark) type locking feature or the like.

Thus, the injector assembly can be used as a blunt injector or, by locking the needle subassembly to the cartridge injector fitting, as a needle syringe injector. The needle subassembly can be provided prepackaged with the other components of the injector assembly or, optionally, separately packaged. Particularly when separately packaged, the needle subassembly would be opened and used only in those instances where intramuscular injection was needed or for other applications requiring a sharp needle injection. Otherwise, the blunt injector subassembly could be used without the needle subassembly attached thereto as a standalone blunt injector for use at a Y-fitting of an intravenous line or the like. Significant reduction can thereby be achieved in the cost of inventory and/or in the inventory storage space requirements. This is especially true in the case of pre-filled injector assemblies. Additional features and advantages of the invention will be understood by those skilled in the art in view of the following detailed description of certain preferred embodiments.

BRIEF DESCRIPTION OF THE DRAWINGS

This invention is further disclosed below by a description of certain preferred embodiments, with reference to the appended drawings wherein.

Figure 1:
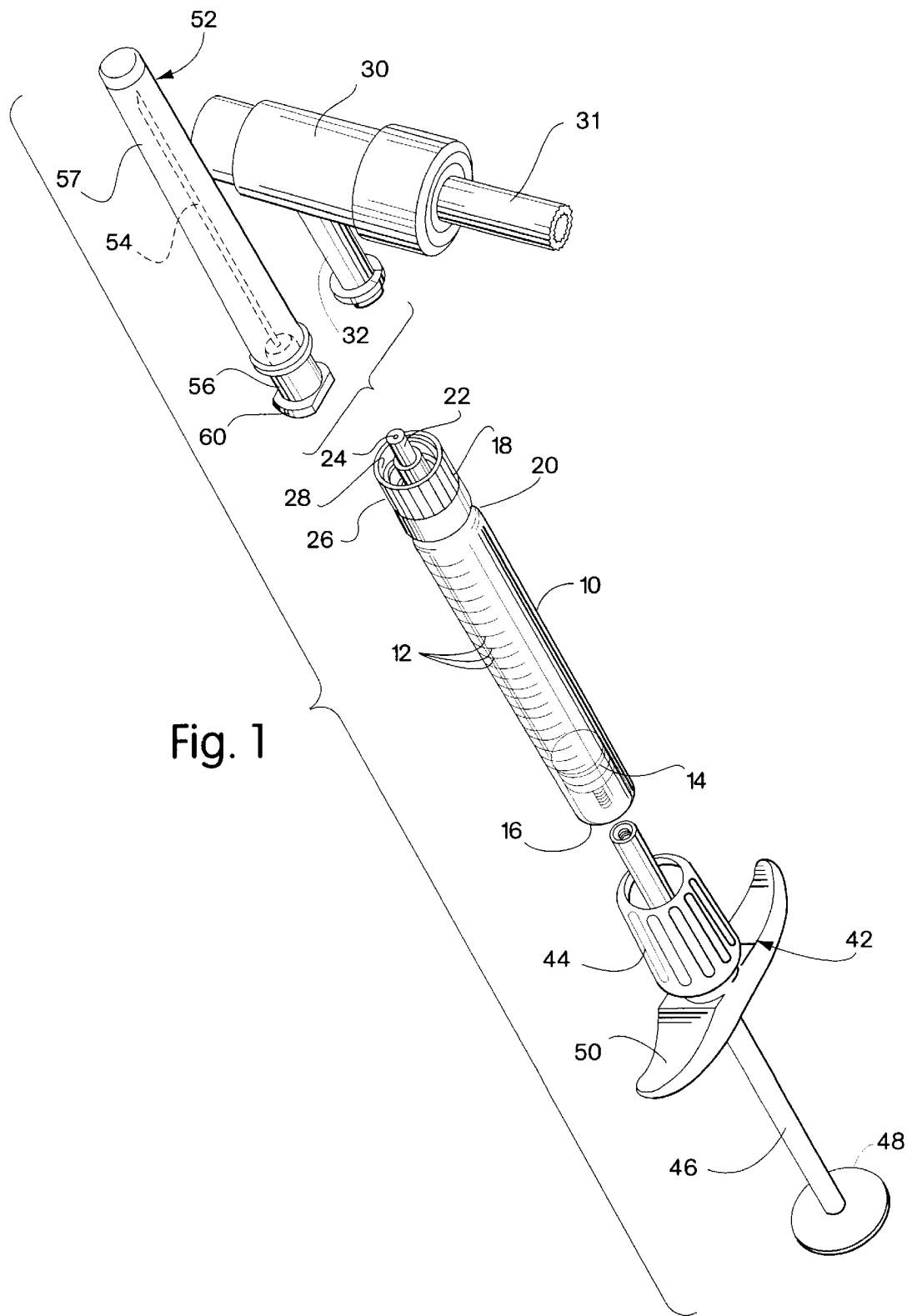
FIG. 1 is an exploded perspective view of a medication injector assembly in accordance with a first preferred embodiment of the invention.

It should be understood that the various embodiments illustrated in the drawings are not necessarily to scale. It will be well within the ability of those skilled in the art, given the benefit of the foregoing disclosure and the following detailed description of preferred embodiments, to select dimensions for a given embodiment which are suitable to the intended application of the device.

DETAILED DESCRIPTION OF CERTAIN PREFERRED EMBODIMENTS

It will be apparent to those skilled in the art that various alternative embodiments are possible for the dual functionality injector assembly disclosed here. In particular, for example, those skilled in the art will recognize that the preferred embodiments discussed below can be configured with alternative and/or additional elements or features to meet the needs of particular applications without departing from the general design and operating principles of the invention. Nevertheless, the particular embodiments described in detail below are seen to be especially preferred for several reasons, including the ease of manufacture and use, as well as their functional reliability. In that regard, those skilled in the art will recognize that in numerous respects the dual functionality injector assembly of these preferred embodiments incorporate certain features compatible with medication administration skills and techniques developed for mono-functionality injector assemblies currently in use.

With respect particularly to the preferred embodiment of FIG. 1, the dual functionality injector assembly is seen to include a tubular shaped cartridge 10 for holding a volume of injectable liquid medication. It should be understood that reference here to liquid medication includes, for example, pharmacologically active medications, as well as amino acid solutions, saline solutions and the like, since the dual functionality injector assembly is suitable for injection of essentially any liquid medication for which current mono-functionality assemblies are used. Cartridge 10 is seen to provide volume markings 12. In addition, a moveable stopper 14 is fitted into the cartridge at its open end 16 to cooperate with the cartridge in containing the liquid medication. If the cartridge is not pre-filled, then stopper 14 may be eliminated.

Injector fitting 18 is provided at front end 20 of cartridge 10, opposite open end 16. Injector fitting 18 is integral with the cartridge, typically being adhesively or otherwise attached. For storage purposes, particularly where the cartridge 10 is pre-filled, injector fitting 18 is fluid-tight prior to use. The injection port discussed further below can be sealed for fluid-tight storage by any suitable means, for example, a removable cap formed of elastomeric material or the like. Alternatively, the injector fitting, if formed of molded plastic, may have a breakaway portion whereby the injection port is exposed.

Referring again to the injector fitting 18, it is seen to provide a blunt injection tip 22 extending axially forward of the cartridge 10. Injection tip 22 has an axial bore 24 providing the aforesaid injection port through which liquid medication within cartridge 10 can be delivered by injection. More specifically, blunt injection tip 22 is sufficiently elongate to operate as a blunt injector through a Y-site or Y-fitting in an intravenous line. In this regard, the blunt injection tip 22 differs fundamentally from the central nipple found in the end fitting of a cartridge in a commonplace mono-functionality needle syringe assembly. The central nipple of such syringe cartridge end fittings are too stubby to allow use of the needle syringe cartridge as a blunt injector at a Y-site, other than perhaps in an emergency situation in which standard medical procedures and requirements are necessarily waived. Injector fitting 18 is seen to further comprise a substantially cylindrical threaded wall 26, preferably having a knurled or otherwise irregular outer surface for improved finger hold. Threaded wall 26 is substantially concentric with the injection tip 22. Injection tip 22, however, extends axially substantially beyond threaded wall 26 for purposes of using the injector assembly as a blunt injector. In the preferred embodiment illustrated in FIG. 1, it is the inside surface 28 of cylindrical wall 26 which is threaded.

Figure 2:
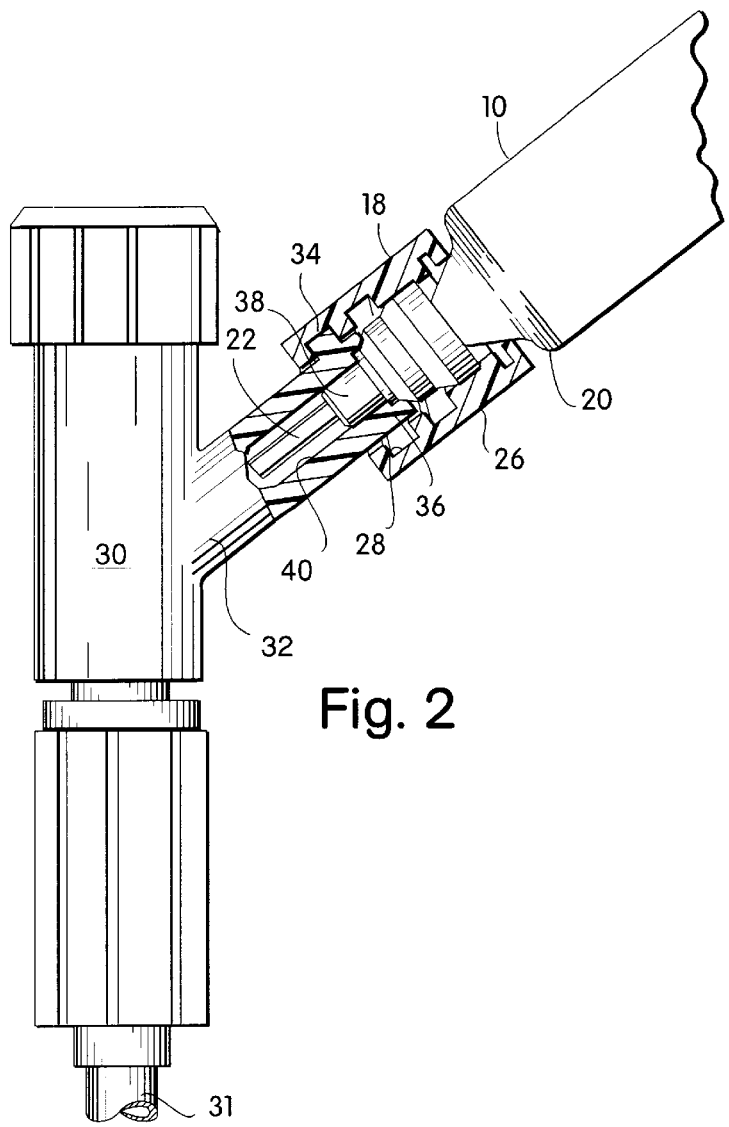
FIG. 2 is an elevation view, partially in cross section and partially broken away, showing the medication injector assembly of FIG. 1 in use as a blunt injector at a Y-fitting of an intravenous line.

The use of the injector assembly as a blunt injector is illustrated in FIG. 2. The injector assembly is there shown to be threadedly connected to a Y-site 30 in an intravenous line 31. It should be recognized that the Y-site and intravenous line do not necessarily form essential elements of the injector assembly, since they are typically provided as separate componentry in medical stocking and distribution channels. Referring again to FIG. 2, Y-site 30 is seen to comprise branch arm 32. A laterally outwardly extending flange 34 is provided at the distal or open end 36 of branch arm 32 which is threadedly received into the injector fitting 18. That is, the threaded inside surface 28 of cylindrical wall 26 of the injector fitting 18 is threadedly mated to distal end 36 as seen in FIG. 2. Blunt injector tip 22 is seen to be received into bore 40 of branch arm 32. In addition, base portion 38 of the injector fitting 18 is received into and forms a fluid-tight seal with the end of bore 40. In this way, the injector assembly of FIG. 1 serves as a blunt injector in accordance with medical standards and practices for operationally secure interconnections of the injector assembly to the Y-site.

Hand-operable plunger 42 is attached to the open end 16 of cartridge 10, preferably in accordance with known design principles. Thus, preferably a collar 44 is provided to be fitted to the end of cartridge 10. Plunger stem 46 is then pushed forward through collar 44 against moveable stopper 14 with the aid of end plate 48 and finger supports 50.

Figure 3:
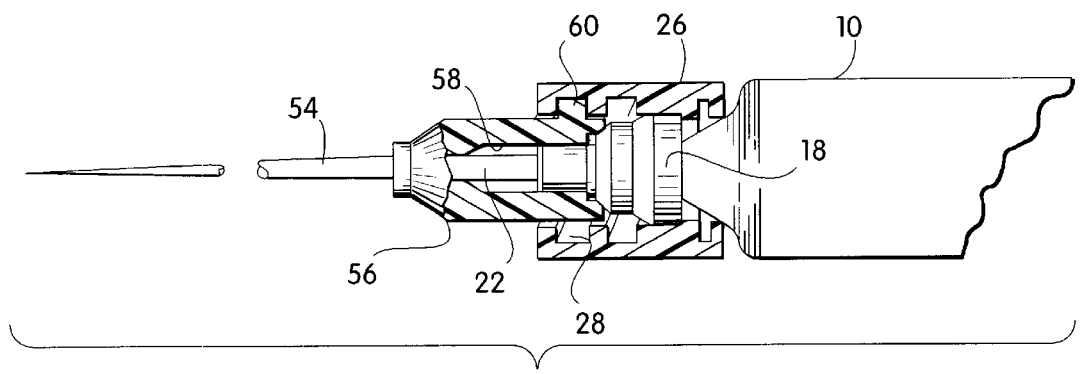
FIG. 3 is an elevation view, partially in cross section and partially broken away, showing the medication injector assembly of FIG. 1 configured as a needle syringe injector.

In accordance with a highly significant aspect of the preferred embodiment of FIG. 1, the injector assembly further comprises a needle subassembly 52 comprising an injection needle 54, preferably having a removable cover or shield 57. Needle 54 is integral with a base 56. The needle subassembly provides a socket to form a fluid-tight, operationally secure interconnection with the injection tip 22 of the injector fitting 18 described above. Additionally, means are provided for locking attachment of the needle subassembly to the injector fitting. In the preferred embodiment of FIG. 1, base 56 is substantially conical and, as best seen in FIG. 3, forms within it a central bore 58 which, at least at its forward end, forms a fluid-tight seal with the end of blunt injection tip 22. By providing the central bore 58 as a chamber configured in a manner corresponding to the end of injection tip 22, a fluid-tight operationally secure interconnection is achieved in the sense that substantially no peripheral air pockets are formed which would be in communication with the fluid flow during injection. Any such peripheral air pockets would be medically disadvantageous, as discussed above.

The needle subassembly 52 further provides means for locking attachment to the injector fitting 18. In accordance with an especially preferred aspect of the embodiment illustrated in FIGS. 1–3, the locking attachment between the needle subassembly and the injector fitting employs the same threaded wall 26 which was employed to form a locking attachment to a Y-site (see FIG. 2) in using the injector assembly as a blunt injector. More specifically, base 56 of needle subassembly 52 has a laterally outwardly extending flange 60 which is threadedly received by threaded inner surface 28 of cylindrical wall 26. The locking means in this respect follows design principles implemented in the commercially well known Luer Lock (trademark). With the needle subassembly mounted to the front end of cartridge 10, the hand-operable plunger 42 is used to deliver liquid medication from the cartridge for intramuscular injections and the like. It will be recognized, therefore, that the injector assembly of FIGS. 1–3 is suitable in a first configuration for use as a blunt injector, and in a second configuration for use as a needle syringe injector with operationally secure interconnections in both configurations and, more generally, in compliance with medical practices and standards.

Figure 4:
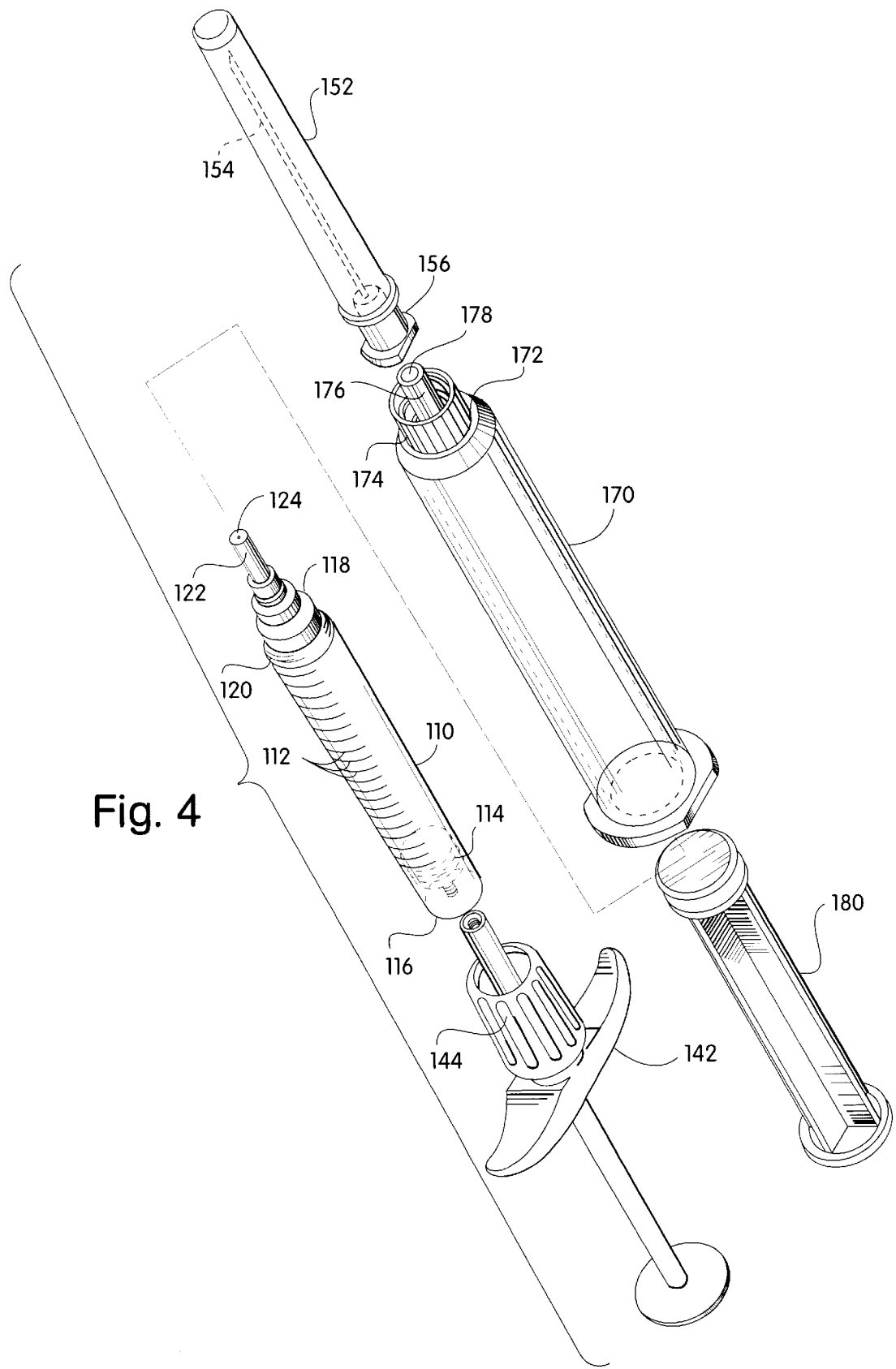
FIG. 4 is an exploded perspective view of a second preferred embodiment of the medication injector assembly of the invention.
Figure 5:
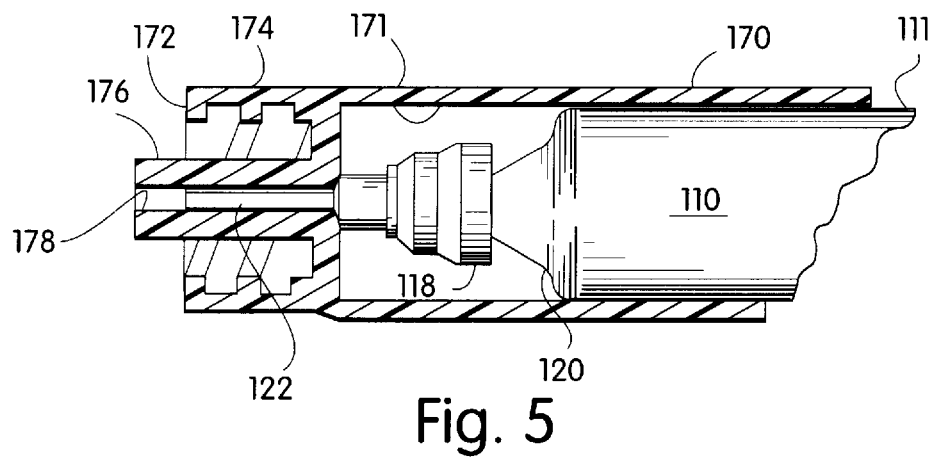
FIG. 5 is an elevation view, partially in cross section and partially broken away, of the embodiments of FIG. 4 in assembly for use as a blunt injector.

An alternative preferred embodiment is illustrated in FIGS. 4 and 5. In FIG. 4, a cartridge 110 corresponding substantially to cartridge 10 of FIG. 1, is seen to provide volume markings 112. A moveable stopper 114 is provided at its open end 116 and an injector fitting 118 is provided at its front end 120. Injector fitting 118 is seen to have an elongate blunt injection tip 122 defining an injection port 124. Blunt injection tip 122 is sufficiently long for use of the injector assembly as a blunt injector in accordance with known techniques. Hand-operable plunger 142 connects by means of collar 144 to the open end 116 of cartridge 110 substantially as described above. For use of the injector assembly of FIGS. 4 and 5 as a needle syringe injector, main cartridge 110 is inserted into an auxiliary outer cartridge 170. Most preferably, the inner surface 171 of outer cartridge 170 forms a sliding or friction fit with the outside surface 111 of main cartridge 110. Outer cartridge 170 has at its front end an end fitting 172 comprising a threaded cylindrical wall 174 and a central nipple 176 coaxial with the threaded wall 174 and with the main body of outer cartridge 170.

With main cartridge 110 inserted into outer cartridge 170, blunt injection tip 122, as best seen in FIG. 5, is received into central bore 178 of nipple 176 to form a fluid-tight connection therewith. A needle subassembly 152 corresponding substantially to the needle subassembly 52 of the embodiment of FIGS. 1–3, is provided for attachment to end fitting 172 of the outer cartridge 170. Employing hand-operable plunger 142, the injector assembly is then operable as a needle syringe injector. It will be recognized in this regard that the blunt injection tip 122 and central nipple 176 are received together, coaxially into the socket formed by base 156 of the needle subassembly 152. Base 156 preferably forms a central bore for this purpose, in fluid communication with the central bore of needle 154.

In accordance with another preferred aspect of the embodiment of FIGS. 4 and 5, hand-operable auxiliary plunger 180 is provided, whereby auxiliary cartridge 170 fitted with needle subassembly 152 may be used as a needle syringe injector assembly without main cartridge 110. Alternatively, in accordance with another preferred embodiment, main plunger 142 is configured to serve as the hand-operable plunger in all three applications of this preferred embodiment.

It will be recognized that the concentric fluid-tight interconnection of blunt injection tip 122 within central bore 178 of the end fitting 172 of the auxiliary 170 is an operationally secure interconnection in that substantially no peripheral air pockets are formed which would be in fluid communication with the liquid medication being injected into a patient. In addition, the aforesaid preferred sliding fit of main cartridge 110 within auxiliary cartridge 170 helps to maintain proper alignment of the blunt injection tip, even against the stresses and forces applied to the assembly during the actual injection of medication.

Figure 6:
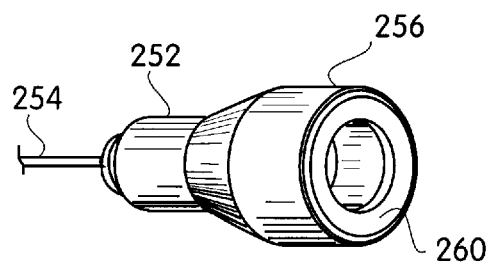
FIG. 6 is a perspective view, partially broken away, of a needle subassembly suitable for use in another preferred embodiment.
Figure 7:
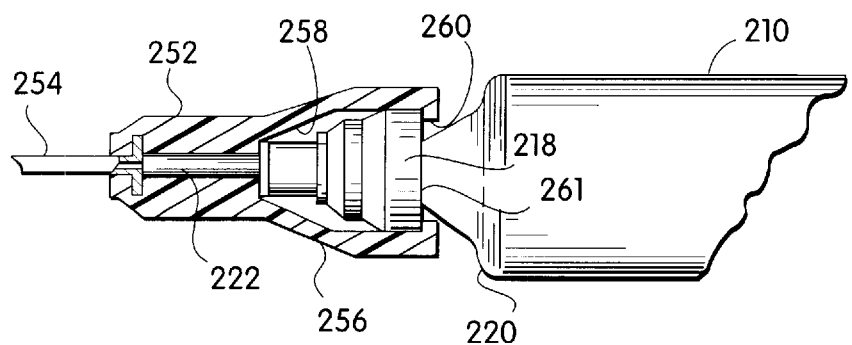
FIG. 7 is a partially schematic view, partially in cross section and partially broken away, of a preferred embodiment of a medication injector assembly of the invention configured with the needle subassembly of FIG. 6 for use as a needle syringe injector.

Another preferred embodiment is illustrated in FIGS. 6 and 7. In this embodiment the means provided by the needle subassembly for locking attachment to the injector fitting comprises a laterally inward extending flange 260. More specifically, the needle subassembly 252 includes a base 256. A needle 254 is integral with base 256 substantially in accordance with embodiments described above. Base 256 forms central bore 258 which receives injector fitting 218 which is integral with the front end 220 of cartridge 210. Blunt injection tip 222 of the injector fitting is received in a fluid tight manner into a correspondingly configured front portion of bore 258. As best seen in FIG. 7, substantially no peripheral air gaps are formed in the medication flow channel from cartridge 210 through needle 254.

Base 256 preferably is formed of an elastomeric material which is sufficiently yielding to expand over the tapered injector fitting 218, whereby inwardly extending lateral flange 260 of the needle subassembly snaps behind injector fitting 218 to sit against rear surface 261 of the injector fitting. Preferably some measure of axially compression is provided by the snap fit of the base 256 of the needle subassembly onto the injector fitting. Those skilled in the art will recognize that base 256 may in the alternative have one or more longitudinally extending cuts to permit flange 260 to bend outwardly over tapered injector fitting 218 as it is first attached. Numerous additional suitable designs for achieving a fluid-tight, operationally secure interconnection between the needle subassembly and the injection tip of the injector fitting will be apparant to those skilled in the art given the benefit of this disclosure.

More generally, it will be apparant to those skilled in the art from this disclosure that numerous additions and alterations can be made to the preferred embodiments discussed above withou departing from the true scope and spirit of the present invention. The following claims are intended to cover such true scope and spirit of the invention.

I claim:

1. A medication injector assembly comprising:
   a syringe, having first and second ends, for holding a volume of injectable liquid medication;
   an injector fitting integral with the first end of the syringe, forming a cylindrical threaded wall and comprising means including a blunt concentric with the threaded wall and having a diameter sized to be received by a Y-site and axially extending sufficiently beyond the cylindrical threaded wall to form a fluid-tight, operationally secure interconnection with a Y-site in an intravenous line;
   a needle subassembly comprising an injection needle integral with a base, the needle subassembly having (a) means for locking attachment to the injector fitting, and (b) a socket sized to form, cooperatively with the cylindrical threaded wall and the means for locking attachment, fluid-tight, operationally secure interconnection with the blunt; and
   a hand-operable plunger means operably connected to the syringe at the second end for forcing injectable liquid from the syringe through the blunt.

2. The medication injector assembly in accordance with claim 1 wherein the base of the needle subassembly has a laterally extending flange receivable by the threaded wall to form said locking attachment of the needle subassembly to injector fitting.

3. The medication injector assembly in accordance with claim 1 wherein the blunt, is an axially extending cylinder of substantially constant cross-sectional diameter, and wherein at least a portion of the socket of the needle sub-assembly is an axially extending tubular passageway having a substantially uniform cross-sectional diameter substantially equal to the cross-sectional diameter of the blunt.

4. The medication injector assembly in accordance with claim 1 wherein the blunt extends axially sufficiently beyond the cylindrical threaded wall to engage an end wall of the socket of the needle subassembly when in fluid-tight, operationally secure interconnection therewith.

5. A medication injector assembly comprising:
   a tubular syringe, having first and second ends, for holding a volume of injectable liquid medication;
   an injector fitting integral with the first end of the syringe, forming a cylindrical threaded wall for threaded attachment to a Y-site in an intravenous line, and a blunt concentric with the threaded wall and having a diameter sized to be received by a Y-site and extending axially substantially beyond the threaded wall sufficiently to form, with the threaded attachment, a fluid-tight, operationally secure interconnection with a Y-site in an intravenous line;
   a needle subassembly comprising an injection needle integral with a base, the needle subassembly having (a) a socket in the base to form a fluid-tight, operationally secure interconnection with the blunt, and (b) means for locking attachment to the injector fitting comprising a flange extending laterally outward from the base, said flange being receivable by the threaded wall to form a threaded attachment; and
   a hand-operable plunger operably connected to the syringe at the second end for forcing injectable liquid from the syringe through the blunt.

6. The medication injector assembly in accordance with claim 5 wherein the blunt, is an axially extending cylinder of substantially uniform cross sectional diameter, and wherein at least a portion of the socket of the needle sub-assembly is an axially extending tubular passageway having a substantially uniform cross-sectional diameter substantially equal to the cross-sectional diameter of the blunt.

7. The medication injector assembly in accordance with claim 5 wherein the blunt extends axially sufficiently beyond the cylindrical threaded wall to engage an end wall of the socket of the needle subassembly when in fluid-tight, operationally secure interconnection therewith.

8. A medication injector assembly comprising:
   a syringe, having first and second ends, for holding a volume of injectable liquid medication;
   an injector fitting integral with the first end of the syringe, forming a blunt adapted to form a fluid-tight, operationally securing interconnection with a Y-site of an intravenous line;
   a needle subassembly comprising an injection needle integral with a base, the needle subassembly having (a) a socket to form a fluid-tight, operationally secure interconnection with the blunt, and (b) means for locking attachment to the injector fitting; and
   a hand-operable plunger means operably connected to the syringe at the second end for forcing injectable liquid from the syringe through the blunt.

9. The medication injector assembly in accordance with claim 8 wherein the blunt, an axially extending cylinder substantially uniform cross-sectional diameter, and wherein at least a portion of the socket of the needle sub-assembly is an axially extending tubular passageway having a substantially uniform cross-sectional diameter substantially equal to the cross-sectional diameter of the blunt.

10. The medication injector assembly in accordance with claim 8 wherein the blunt extends axially sufficiently beyond the cylindrical threaded wall to engage an end wall of the socket of the needle subassembly when in fluid-tight, operationally secure interconnection therewith.

* * * * *